United States Patent
Zhang et al.

(10) Patent No.: US 11,969,145 B2
(45) Date of Patent: Apr. 30, 2024

(54) MEDICAL ENDOSCOPE IMAGE RECOGNITION METHOD AND SYSTEM, AND ENDOSCOPIC IMAGING SYSTEM

(71) Applicant: TENCENT TECHNOLOGY (SHENZHEN) COMPANY LIMITED, Guangdong (CN)

(72) Inventors: Zijian Zhang, Shenzhen (CN); Zhongqian Sun, Shenzhen (CN); Xinghui Fu, Shenzhen (CN); Hong Shang, Shenzhen (CN); Xiaoning Wang, Shenzhen (CN); Wei Yang, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 352 days.

(21) Appl. No.: 17/446,095

(22) Filed: Aug. 26, 2021

(65) Prior Publication Data

US 2021/0390693 A1 Dec. 16, 2021

Related U.S. Application Data

(63) Continuation of application No. PCT/CN2020/087184, filed on Apr. 27, 2020.

(30) Foreign Application Priority Data

May 6, 2019 (CN) .......................... 201910372711.4

(51) Int. Cl.
*A61B 1/00* (2006.01)
*G06T 7/00* (2017.01)

(52) U.S. Cl.
CPC .. *A61B 1/000094* (2022.02); *A61B 1/000096* (2022.02); *A61B 1/0005* (2013.01);
(Continued)

(58) Field of Classification Search
CPC ............ A61B 1/0005; A61B 1/000094; A61B 1/000096; G06T 7/0012;
(Continued)

(56) References Cited

U.S. PATENT DOCUMENTS

2007/0015989 A1* 1/2007 Desai .................. A61B 5/0084
600/407
2014/0350395 A1 11/2014 Shachaf et al.
(Continued)

FOREIGN PATENT DOCUMENTS

| CN | 105354852 | 2/2016 |
|---|---|---|
| CN | 107240091 | 10/2017 |

(Continued)

OTHER PUBLICATIONS

Park "Colonoscopic polyp detection using convolutional neural networks", Progress in Biomedical Optics and Imageing, SPIE—International Society for Optics Engineering, vol. 9785, Mar. 24, 2016, pp. 978528-1-978528-6, XP60070513, ISSN: 1605-7422, DOI: 10.1117/12.2217148, ISBN: 978-1-5106-0027-0. (Year: 2016).*

(Continued)

*Primary Examiner* — John J Lee
(74) *Attorney, Agent, or Firm* — ARENTFOX SCHIFF LLP

(57) ABSTRACT

A medical endoscope image recognition method is provided. In the method, endoscope images are received from a medical endoscope. The endoscope images are filtered with a neural network, to obtain target endoscope images. Organ information corresponding to the target endoscope images is recognized via the neural network. An imaging type of the target endoscope images is identified according to the corresponding organ information with a classification network. A lesion region in the target endoscope images is localized according to an organ part indicated by the organ informa- (Continued)

tion. A lesion category of the lesion region in an image capture mode of the medical endoscope corresponding to the imaging type is identified.

20 Claims, 8 Drawing Sheets

(52) U.S. Cl.
CPC .. *G06T 7/0012* (2013.01); *G06T 2207/10068* (2013.01); *G06T 2207/20024* (2013.01); *G06T 2207/20081* (2013.01); *G06T 2207/20084* (2013.01); *G06T 2207/30092* (2013.01); *G06T 2207/30096* (2013.01)

(58) Field of Classification Search
CPC . G06T 2207/10068; G06T 2207/20024; G06T 2207/20081; G06T 2207/20084; G06T 2207/30092; G06T 2207/30096
See application file for complete search history.

(56) References Cited

U.S. PATENT DOCUMENTS

| | | | |
|---|---|---|---|
| 2015/0294463 | A1 | 10/2015 | Takahashi |
| 2018/0225820 | A1* | 8/2018 | Liang ..................... G16H 20/40 |
| 2021/0186315 | A1* | 6/2021 | Oosake ............ A61B 1/000096 |

FOREIGN PATENT DOCUMENTS

| | | |
|---|---|---|
| CN | 107564580 A | 1/2018 |
| CN | 107610187 | 1/2018 |
| CN | 107625513 | 1/2018 |
| CN | 109447973 | 3/2019 |
| CN | 109447987 | 3/2019 |
| CN | 110136106 | 8/2019 |
| EP | 1806091 | 7/2007 |
| WO | 2018/160288 | 9/2018 |

OTHER PUBLICATIONS

Supplementary European Search Report dated Jun. 3, 2022 in Application No. 20802793.8, pp. 1-9.
Park Sun Young et al: "Colonoscopic polyp detection using convolutional neural networks", Progress in Biomedical Optics and Imaging, SPIE—International Society for Optical Engineering, Bellingham, WA, US, vol. 9785, Mar. 24, 2016, pp. 978528-978528.
Pogorelov Konstantin et al: "Efficient disease detection in gastrointestinal videos—global features versus neural networks", Multimedia Tools and Applications, Kluwer Academic Publishers, Boston, US, vol. 76, No. 21, Jul. 19, 2017 (Jul. 19, 2017) , pp. 22493-22525.
International Search Report dated Aug. 11, 2020 in Application No. PCT/CN2020/087184. (8 pages).
Written Opinion dated Aug. 11, 2020 in International Application No. PCT/CN2020/087184. (6 pages).
Chinese Office Action dated Aug. 26, 2020 in Application No. 2019107565015. (13 pages).
Cao et al., "Application of Narrow Band Imaging Combined with Lugol Chromo-Endoscopy in the Diagnosis of Advanced Esophageal Carcinoma," Chinese Journal of Digestive Surgery, vol. 12, No. 10, Oct. 31, 2013 (4 pages).
Jie Li et al., "Micro-Vision of Capsule Robot Based on Color Image Interpolation Algorithm," Feb. 28, 2014 (5 pages).
Obukhova, "Review of Noise Reduction Methods and Estimation of their Effectiveness for Medical Endoscopic Images Processing," 2018 22nd Conference of Open Innovations Association (FRUCT), Sep. 20, 2018 (7 pages).
Hiroyasu, "Preprocessing with image denoising and histogram equalization for endoscopy image analysis using texture analysis," 2015 37th Annual International Conference of the IEEE Engineering in Medicine and Biology Society (EMBC), Nov. 5, 2015 (4 pages).
Xiaoguang Ru et al., "Simulation and Analysis of Lesions Characteristic Rapid Positioning Algorithm with Endoscope Images," Computer Simulation, Feb. 28, 2013 (13 pages).

* cited by examiner

MEDICAL ENDOSCOPE IMAGE RECOGNITION METHOD AND SYSTEM, AND ENDOSCOPIC IMAGING SYSTEM

RELATED APPLICATIONS

This application is a continuation of International Application No. PCT/CN2020/087184, entitled "MEDICAL ENDOSCOPE IMAGE IDENTIFICATION METHOD AND SYSTEM, AND ENDOSCOPE IMAGE SYSTEM" and filed on Apr. 27, 2020, which claims priority to Chinese Patent Application No. 201910372711.4, entitled "MEDICAL ENDOSCOPE IMAGE RECOGNITION METHOD AND SYSTEM, DEVICE, AND ENDOSCOPIC IMAGING SYSTEM" and filed May 6, 2019. The entire disclosures of the prior applications are hereby incorporated by reference in their entirety.

FIELD OF THE TECHNOLOGY

Embodiments of this disclosure relate to the field of computer application technologies, including a medical endoscope image recognition method and system, and an endoscopic imaging system.

BACKGROUND OF THE DISCLOSURE

Various category identifications executed based on deep learning are generally important tools for solving classification for a large amount of data in various application scenarios. For example, in application scenarios such as image and natural language processing, large-scale classification and recognition of a large amount of data may be implemented, so as to rapidly and accurately obtain a related classification prediction result and accelerate the implementation of functions in the application scenarios.

During classification prediction performed on images, for different deployed application scenarios, images for classification prediction and methods for classification prediction are also different from one another. Taking Artificial Intelligence (AI)+a medical scenario as an example, with continuously photographing in the alimentary canal by the endoscope, a large quantity of endoscope images are formed, the classification prediction method is thus required to classify and recognize the large quantity of endoscope images.

However, the related medical image has a single classification prediction function, which cannot be adapted to the whole process of photographing by the endoscope for generating a medical endoscope video stream; moreover, since capturing the medical endoscope image would be unavoidably affected by switching and shaking of the endoscope, and during photographing, a lens of the endoscope would unavoidably encounter various liquids and foreign matters, the obtained endoscope image would often have a large amount of interference and noise, rendering weak robustness. Hence, it is expected to provide a method and system for recognizing a medical endoscope image, so that photographing by the endoscope in the alimentary canal can be adapted to the whole photographing process and the robustness is relatively strong.

SUMMARY

To resolve the technical problems in the related art that classification prediction of medical images cannot be adapted to the whole process of capturing medical endoscope images by an endoscope and the robustness is weak, embodiments of this disclosure include a medical endoscope image recognition method and system, an endoscopic imaging system, and medical endoscope image recognition.

A medical endoscope image recognition method is provided. In the method, endoscope images are received from a medical endoscope. The endoscope images are filtered with a neural network, to obtain target endoscope images. Organ information corresponding to the target endoscope images is recognized via the neural network. An imaging type of the target endoscope images is identified according to the corresponding organ information with a classification network. A lesion region in the target endoscope images is localized according to an organ part indicated by the organ information. A lesion category of the lesion region in an image capture mode of the medical endoscope corresponding to the imaging type is identified.

A medical endoscope image recognition system is provided. The medical endoscope image recognition system includes processing circuitry configured to receive endoscope images from a medical endoscope, and filter the endoscope images with a neural network, to obtain target endoscope images. The processing circuitry is configured to recognize organ information corresponding to the target endoscope images via the neural network, and identify an imaging type of the target endoscope images according to the corresponding organ information with a classification network. Further, the processing circuitry is configured to localize a lesion region in the target endoscope images according to an organ part indicated by the organ information; and identify a lesion category of the lesion region in an image capture mode of the medical endoscope corresponding to the imaging type.

A machine device is provided, including a processor and a memory. The memory stores computer-readable instructions, the computer-readable instructions, when executed by the processor, can implement the foregoing medical endoscope image recognition method.

A non-transitory computer-readable storage medium is provided. The non-transitory computer-readable storage medium stores instructions which when executed by a processor cause the processor to perform the foregoing medical endoscope image recognition method.

An endoscopic imaging system is provided. The endoscopic imaging system includes the medical endoscope image recognition system, and a display device configured to display the endoscope images.

An endoscopic imaging system is provided. The endoscopic imaging system includes a display device for a medical endoscope video and a work station. The workstation can be configured to implement the foregoing medical endoscope image recognition method by using a medical endoscope video stream outputted by an endoscope as an input.

The technical solutions provided in the embodiments of this disclosure may include the following beneficial effects:

For a given medical endoscope video stream, first original endoscope images are obtained therefrom, and then the obtained original endoscope image are filtered by using a neural network to obtain target endoscope images, to eliminate a large amount of interference existing under the condition of switching and shaking during the photographing by the endoscope and encountering various liquids and foreign matters, so that robustness is enhanced.

After filtering the original endoscope images, corresponding organ information is recognized from the generated target endoscope image, so as to identify an image type suitable for the target endoscope images according to the corresponding organ information by using a classification network, and finally, in a photographing mode corresponding to the image type, according to a part indicated by the organ information, a lesion region is localized and the lesion category thereof is identified to implement the classification prediction for the whole photographing process of the endoscope in the alimentary canal, and systematic and complete image recognition is implemented.

It is to be understood that the foregoing general descriptions and the following detailed descriptions are only exemplary, and cannot be limited in the embodiments of this application.

BRIEF DESCRIPTION OF THE DRAWINGS

The accompanying drawings, which are incorporated herein and constitute a part of this specification, illustrate embodiments consistent with this disclosure and, together with the specification, serve to explain the principles of the embodiments of this disclosure.

DESCRIPTION OF EMBODIMENTS

Exemplary embodiments are described in detail herein, and examples of the exemplary embodiments are shown in the accompanying drawings. When the following descriptions are made with reference to the accompanying drawings, unless otherwise indicated, the same numbers in different accompanying drawings represent the same or similar elements. The implementations described in the following exemplary embodiments do not represent all implementations consistent with embodiments of this disclosure. On the contrary, the implementations are merely examples of apparatuses and methods consistent with those are described in detail in the appended claims and some aspects of the embodiments of this disclosure.

Figure 1:
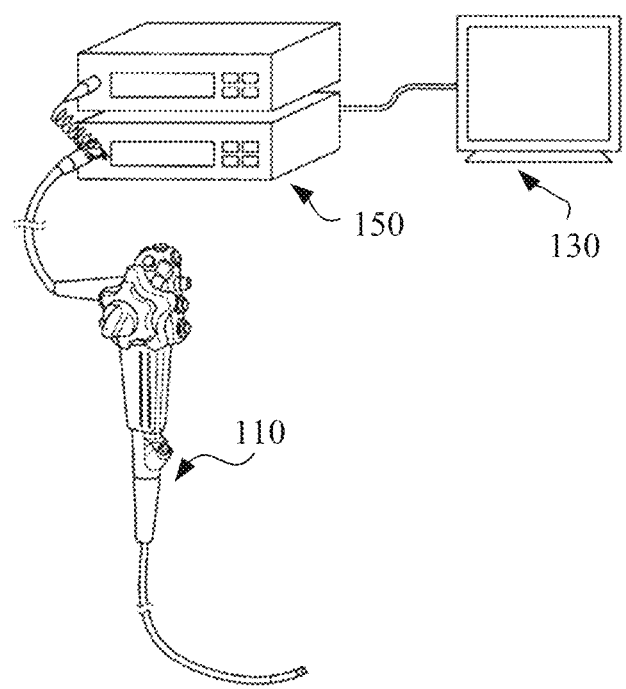
FIG. 1 is a schematic diagram of an implementation environment according to an embodiment of this disclosure.

FIG. 1 is a schematic diagram of an implementation environment according to an embodiment of this disclosure. In an exemplary embodiment, the implementation environment includes an endoscopic imaging system including an endoscope 110, a display device 130, and a workstation 150. The endoscope 110 is used as a data source for image recognition; along with the movement and photographing of the endoscope 110 in alimentary canals, the display device 130 continuously displays video images. For example, the images are displayed by using each endoscope image frame captured by the endoscope 110.

On this basis, the image captured by the alimentary canal endoscope in this embodiment of this disclosure is also recognized by using the workstation 150, so as to examine the alimentary canal endoscope, to implement systematic and comprehensive classification prediction, thereby obtaining lesion region distribution in the endoscope image and a category of the distributed lesion region.

The workstation 150 is a host deployed for the endoscope, such as a micro-computer with a large or small volume that only needs to meet performance requirements.

Hence, this disclosure includes a physical medical device, such as an endoscopic imaging system, which at least includes: a display device for a medical endoscope video and a workstation, implementing the following embodiments of the medical endoscope image recognition method by using a medical endoscope video stream outputted by an endoscope as an input.

Exemplarily, in the endoscopic imaging system, the medical endoscope video stream inputted to the workstation may be currently captured in real time by the endoscope, and may also be obtained by photographing at any time, which is not limited herein.

In an exemplary embodiment, the endoscopic imaging system also includes an endoscope; the accessed endoscope provides a data source for the workstation, and then the endoscope inputs the medical endoscope video to the workstation, so as to implement real-time recognition of a video image.

Figure 2:
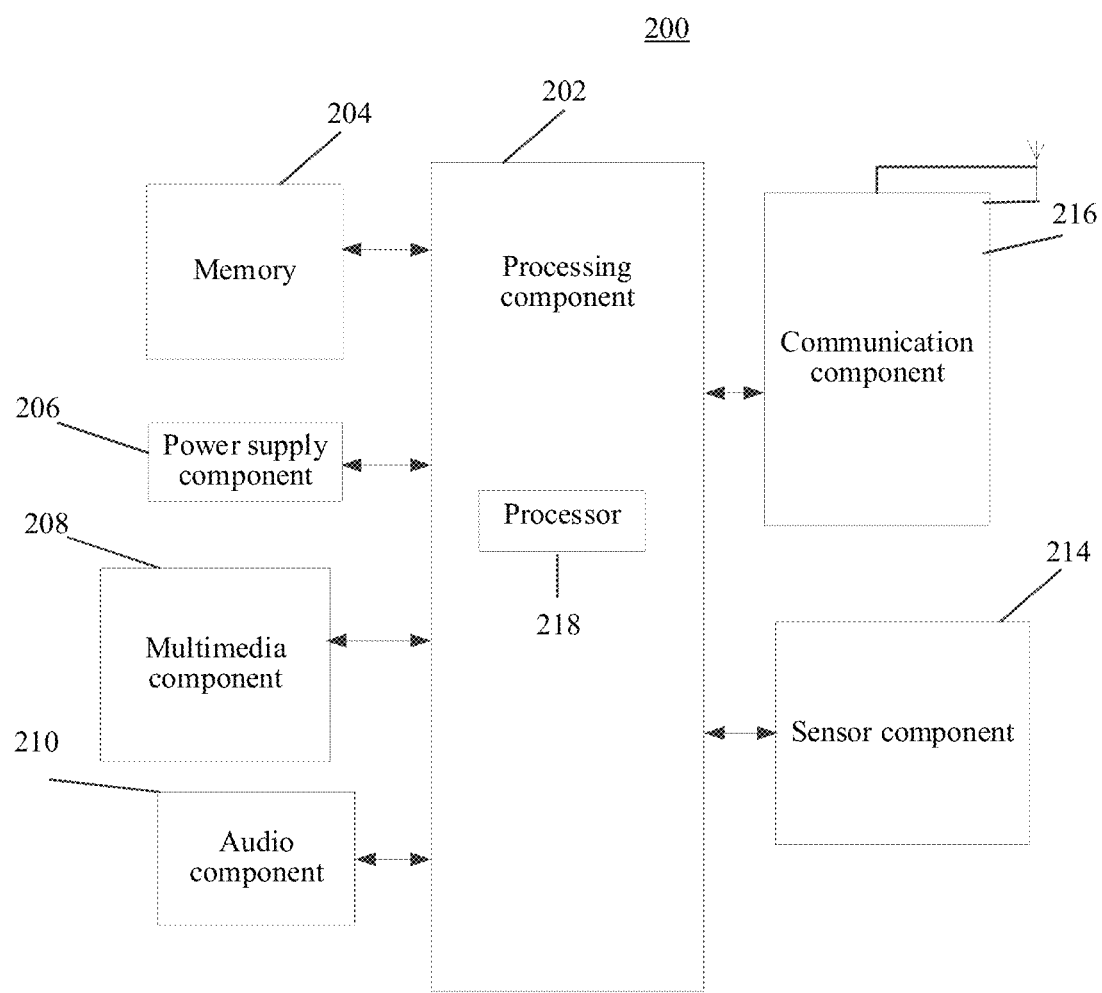
FIG. 2 is a block diagram of an apparatus according to an exemplary embodiment.

FIG. 2 is a block diagram of an apparatus according to an exemplary embodiment. For example, the apparatus 200 may be a workstation 150 in an implementation environment shown in FIG. 1. The workstation 150 may be a micro-computer in any form as long as it meets the performance requirements. For example, the workstation 150 may be a host connected to an endoscope.

Referring to FIG. 2, the apparatus 200 includes at least the following components: a processing component 202, a memory 204, a power supply component 206, a multimedia component 208, an audio component 210, a sensor component 214, and a communication component 216.

The processing component 202 generally controls integral operations of the apparatus 200, such as operations related to displaying, a phone call, data communication, a camera operation, and a record operation. The processing component 202 includes processing circuitry such as at least one or more processors 218 to execute instructions, to implement all or some steps of the following method. In addition, the processing component 202 includes at least one or more modules, to facilitate the interaction between the processing component 202 and other components. For example, the processing component 202 may include a multimedia module, to facilitate the interaction between the multimedia component 208 and the processing component 202.

The memory 204 is configured to store various types of data to support operations on the apparatus 200. Examples of the types of data include instructions of any application program or method to be operated on the apparatus 200. The memory 204 is at least implemented by using a volatile or non-volatile storage device of any type or a combination thereof, for example, a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a disk, or an optical disc. The memory 204 further stores one or more modules, and the one or more modules are configured to be executed by the one or more processor 218, to implement all or some steps of the following method shown in any of FIG. 3, FIG. 4, FIG. 5, FIG. 6, FIG. 7, FIG. 8, FIG. 9, and FIG. 10.

The power supply component 206 provides power to various components of the apparatus 200. The power supply component 206 includes at least a power supply management system, one or more power supplies, and other components associated with generating, managing and allocating power for the apparatus 200.

The multimedia component 208 includes a screen providing an output interface between the apparatus 200 and a user. In some embodiments, the screen may include a liquid crystal display (LCD) and a touch panel. If the screen includes the touch panel, the screen may be implemented as a touchscreen to receive an input signal from the user. The touch panel includes one or more touch sensors to sense a touch, a slide, and a gesture on the touch panel. The touch sensor may not only sense the boundary of touching or sliding operations, but also detect duration and pressure related to the touching or sliding operations. The screen further includes an organic light emitting diode (OLED) display.

The audio component 210 is configured to output and/or input an audio signal. For example, the audio component 210 includes a microphone (MIC). When the apparatus 200 is in an operating mode, such as a call mode, a record mode, and a speech recognition mode, the microphone is configured to receive an external audio signal. The received audio signal may further be stored in the memory 204 or be sent by using the communication component 216. In some embodiments, the audio component 210 further includes a speaker, configured to output an audio signal.

The sensor component 214 includes one or more sensors, configured to provide status evaluation in each aspect to the apparatus 200. For example, the sensor component 214 detects a power-on/off state of the apparatus 200 and a relative location of a component. The sensor component 214 further detects changes in a location of the apparatus 200 or a component of the apparatus 200 and a temperature change of the apparatus 200. In some embodiments, the sensor component 214 further includes a magnetic sensor, a pressure sensor or a temperature sensor.

The communication component 216 is configured to facilitate communication in a wired or wireless manner between the apparatus 200 and other devices. The apparatus 200 accesses a communication standard-based wireless network, such as Wi-Fi. In an exemplary embodiment, the communication component 216 receives, by using a broadcast channel, a broadcast signal or broadcast-related information from an external broadcast management system. In an exemplary embodiment, the communication component 216 further includes a near field communication (NFC) module to facilitate short-distance communication. For example, the NFC module may be implemented based on a radio frequency identification (RFID for short) technology, an Infrared Data Association (IrDA for short) technology, an ultra wideband (UWB) technology, a Bluetooth technology, and another technology.

In an exemplary embodiment, the apparatus 200 is implemented by using processing circuitry such as one or more application-specific integrated circuits (ASICs), a digital signal processor, a digital signal processing device, a programmable logic device, a field-programmable gate array, a controller, a micro controller, a microprocessor, or other electronic elements, and is configured to perform the following method.

Figure 3:
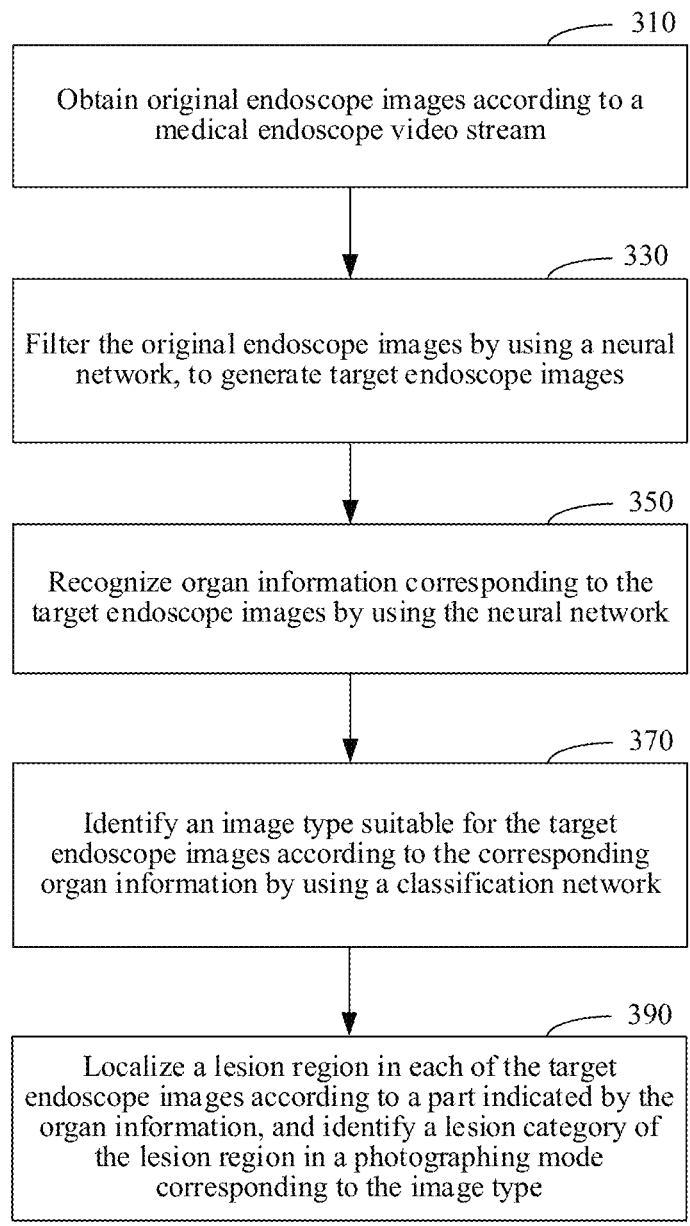
FIG. 3 is a flowchart of a medical endoscope image recognition method according to an exemplary embodiment.

FIG. 3 is a flowchart of a medical endoscope image recognition method according to an exemplary embodiment, taking the workstation executing the method according to FIG. 1 as an example. In an exemplary embodiment, the medical endoscope image recognition method, as shown in FIG. 3, can include at least the following steps.

In step 310, original endoscope images are obtained according to a medical endoscope video stream.

The medical endoscope video stream is a video stream captured by an endoscope in a medical environment, for example, a real hospital usage environment. During the movement and photographing of the endoscope, the medical endoscope video stream presents video endoscopy captured by a lens of the endoscope. Hence, original endoscope image frames can be obtained according to the medical endoscope video stream. Since each original endoscope image frame describes the video endoscopy captured by the endoscope at a time point, based on each original endoscope image frame, the medical endoscope image can be recognized.

As can be understood, during the implemented medical endoscope image recognition, an endoscope captures the medical endoscope video stream in an organism, for example, a human body. Exemplarily, the endoscope captures the medical endoscope video stream in a tract communicated with the outside or a sealed body cavity. For example, the indicated tract communicated with the outside may be an alimentary canal, a respiratory tract, a urinary tract, and the like; the sealed body cavity may be a cavity body that needs an incision for the endoscope to be fed such as chest, an abdominal cavity, and a joint cavity. Capturing and recognizing the medical endoscope video stream by using the endoscope can obtain organ conditions in the corresponding tract.

In the process of using the endoscope to examine the tract, the obtained medical endoscope video stream is inputted to the workstation for recognizing the medical endoscope image. Besides, the medical endoscope video stream obtained before, for example, a historical medical endoscope video stream, may also be subjected to the medical endoscope image recognition. That is, recognition may be performed based on a real-time captured image, and may also be performed based on a large quantity of stored medical endoscope video streams. The medical endoscope video stream obtained through real-time photographing by the endoscope in the alimentary canal is taken as an example for detailed explanations below.

In the process of using the endoscope to examine the alimentary canal, the obtained medical endoscope video stream is inputted to the workstation, and the corresponding original endoscope image is obtained from the current alimentary canal image, for real-time recognition based on the original endoscope image.

As can be understood, the current image displayed by the display device 130 of the endoscopic imaging system is the alimentary canal image. Along with the movement and photographing of the endoscope in alimentary canals, the display device 130 displays the video of alimentary canal images through the inputted medical endoscope video stream, and at this time, the original endoscope image required by image recognition is obtained from the current image. The original endoscope image is an original image directly obtained under the photographing by the endoscope, and on this basis, the medical endoscope image is recognized.

In an exemplary embodiment, step 310 includes: obtaining the original endoscope images from the inputted medical endoscope video stream along with movement and photographing of the endoscope in the tract or the sealed body cavity.

The tract communicated with the outside and the sealed tract do not only have a single organ; taking the alimentary canal as an example, the alimentary canal includes a plurality of sub-organs, such as stomach, esophagus, pharynx and duodenum. During examination of the alimentary canal, the endoscope moves and continuously takes photos in the alimentary canal so as to obtain a video stream related to the sub-organs. Accordingly, the original endoscope images constituting the video stream are images related to the sub-organ where the endoscope is located, and indicate the state of the sub-organ.

It is explained that when examining the tract, with the movement and continuous photographing of the endoscope, the photographing of the sub-organ where the endoscope is located is not limited to a single original endoscope image; that is, a plurality of original endoscope images obtained all correspond to one sub-organ, and therefore, the subsequent recognition of the medical endoscope image using the original endoscope images as inputs actually relates to classification prediction of the sub-organ where the endoscope is located.

In another exemplary embodiment, the inputted medical endoscope video stream is not obtained through real-time photographing. For example recognition of the medical endoscope image according to this embodiment of this disclosure is conducted based on the stored medical endoscope video streams. In this scenario, step 310 can include:
  obtaining the stored medical endoscope video stream; and
  obtaining the original endoscope images from the medical endoscope video stream, the original endoscope image being used for recognizing a lesion region in a tract or a sealed body cavity photographed by an endoscope and identifying a lesion category of the lesion region.

The stored medical endoscope video stream is recognized one by one using the medical endoscope image recognition method provided by the embodiments of this disclosure, so as to recognize the lesion region and lesion category of the organ part related to the original endoscope image, to implement the processing of a large quantity of historical medical endoscope video streams.

In this exemplary embodiment, the medical endoscope video stream is no longer obtained through the output of the endoscope, but the stored medical endoscope video streams are obtained, so as to obtain the original endoscope image therefrom.

Through the implementation of this exemplary embodiment, a large quantity of stored medical endoscope video streams can also be recognized so as to facilitate medical research, and provide automatic video image recognition for the real medical environment.

In step 330, the original endoscope images are filtered by using a neural network, to generate target endoscope images.

First, it is to be explained that, all the original endoscope images obtained from the medical endoscope video stream need to be filtered to filter out the interference in the images. As can be understood, not all of the large quantity of original endoscope images obtained from the medical endoscope video stream can be used for the recognition of the medical endoscope images, some of which cannot be used for the recognition due to influences caused by various factors during photographing; these images would exist as interference and thus need to be filtered out, such as the original endoscope images obtained by photographing during switching, shaking, or switching and shaking of the endoscope and the original endoscope images obtained when a lens encounters various liquids and foreign matters during photographing. These original endoscope images are low-quality images, exist as interferences for the recognition, and need to be recognized and filtered out by using the neural network.

For example, whether the obtained original endoscope images are the low-quality images is recognized by using the neural network and the original endoscope images that are the low-quality images are filtered out. Accordingly, the used neural network is obtained through training by using the low-quality images as examples.

In the process of actual usage of the endoscope, since the endoscope would unavoidably be switched and shaken in the alimentary canal and a photographing lens would also unavoidably encounter various liquids and foreign matters, the original endoscope images obtained through photographing include a large quantity of low-quality and noisy images. Recognizing and filtering the low-quality images from the original endoscope images obtained in step 310 by using the neural network shields the influence on image recognition by the low-quality images, greatly improving the robustness. In addition, useless and unnecessary images are filtered out in advance through recognizing and filtering the low-quality images, so that computing resources consumed by executing the follow-up steps are reduced, and therefore, speed and real-time performance can be effectively improved.

The low-quality image recognition performed on the original endoscope images is implemented by using the trained neural network. Moreover, this neural network is trained according to endoscope image samples that are the low-quality images and endoscope image samples that are the non-low-quality images. The trained neural network can output, for the inputted original endoscope image, a probability of being the low-quality image and a probability of being the non-low-quality image, so as to finally determine whether the original endoscope image is the low-quality image or the non-low-quality image; the original endoscope image determined to be the low-quality image is filtered out and no follow-up steps are adopted for processing.

Recognition of the low-quality images for the obtained multiple original endoscope images is conducted by using the neural network, to filter out the low-quality images included in the obtained multiple original endoscope images, complete filtering of the low-quality images, and generate target endoscope images, so as to recognize organ parts that the endoscope enters.

In an exemplary embodiment, the original endoscope images inputted into the neural network for low-quality image recognition are necessarily adapted to the neural network to ensure consistency and accuracy of actual prediction. Hence, before predicting the low-quality images, pre-processing the original endoscope images is further required, for example, size adjusting, cutting, and the like, to obtain the original endoscope images with the size adapted to the neural network.

The target endoscope images are the remaining original endoscope images after eliminating the low-quality images in the original video images. At this point, by filtering the original endoscope images, the generated target endoscope images can shield interference, reduce a data amount, and also enhance the accuracy of recognition.

It is to understood that, when filtering the original endoscope images, for the low-quality images and the non-low-quality images for training the neural network, two major categories of the original endoscope images are relative, regarding required different filtering precision, the same original endoscope image may be a low-quality image and may also be a non-low-quality image.

In step 350, organ information corresponding to the target endoscope images is recognized by using the neural network.

As the movement and continuously photographing in the tract by the endoscope, the endoscope is located in the tract, for example, on a certain sub-organ in the alimentary canal, however, the endoscope would not output the organ part where it is located, the organ part is often required to be recognized by checking using the endoscope image in a manual way, so as to facilitate the implementation of accurate classification prediction of the endoscope image for the organ part where the endoscope is located.

Moreover, in the recognition implemented by this exemplary embodiment, for the target endoscope image generated through filtering the low-quality image, the alimentary canal part where the endoscope is currently located is recognized. For example recognition is performed to obtain the organ information corresponding to the target endoscope image, and the organ information indicates the organ part in the tract where the endoscope is located when capturing the target endoscope image.

In an exemplary embodiment, recognizing the organ information of the target endoscope image is also implemented by using the constructed neural network; the target endoscope image is used as an input, and information of an organ where the endoscope is located when capturing the target endoscope image is outputted.

For example, using the alimentary canal as an example, the constructed neural network may by a four-class network. To be adapted to the sub-organs on the alimentary canal, such as stomach, esophagus, pharynx and duodenum, the four-class network is pre-constructed, to recognize the target endoscope image so as to recognize an organ location where the endoscope is located.

Accordingly, the four-class network is obtained by training using the original endoscope image in which corresponding alimentary canal parts, that is the sub-organs on the alimentary canal, are annotated. The four-class network adapted to the alimentary canal parts executes the recognition of the alimentary canal part where the endoscope is currently located, the endoscope images for network training, such as samples of the four-class network that cover all the alimentary canal parts, and therefore, it is no longer limited to the recognition of a single sub-organ, thereby enhancing the recognition performance of an image captured by the endoscope on the alimentary canal.

In step 370, an image type suitable for the target endoscope images is identified according to the corresponding organ information by using a classification network.

Through executing the steps above, after localizing the organ part and recognizing the organ information on the target endoscope image, according to the organ information, the photographing mode for the target endoscope image can be switched.

The image type to which the target endoscope image is adapted is an image type that can best enhance the image endoscopy in the target endoscope image. Through identifying the image type, the most proper photographing mode can be determined for the target endoscope image. For example, based on the image type, the photographing mode corresponding to the image type can be switched.

Exemplarily, the recognition of the image type to which the target endoscope image is adapted is implemented by using the classification network. In an exemplary embodiment, corresponding to image type division, the classification network may be a three-class network, that is a classification network that divides images into three image types, so as to implement the recognition of the target endoscope image for the three image types.

It is to be understood that different photographing modes correspond to different image types, and therefore, when the photographing modes are set as three, such as white light, Narrow Band Imaging (NBI), and iodine dyeing modes, three corresponding image types exist. Hence, the photographing mode to which an image content in the target endoscope image is adapted can be determined through the recognition of the image type, that is the photographing mode corresponding to the image type can be identified.

For example, according to the alimentary canal part indicated in the organ information and the image content of a suspicious lesion or disease lesion region in the target endoscope image, through the recognition of the neural network, it is obtained that the target endoscope image is the image type corresponding to the NBI, and the image type corresponds to the NBI photographing mode.

In step 390, a lesion region in each of the target endoscope images is localized according to a part indicated by the organ information, and a lesion category of the lesion region in the photographing mode corresponding to the image type is identified.

During the execution of the preceding steps, after the sub-organ where the endoscope is located when photographing the target endoscope image is known, for example the organ part where it is located is determined, the target endoscope image in the photographing mode to which the target endoscope image corresponding to the sub-organ can be obtained, so as to implement the localization of the lesion region and the recognition of the lesion category of the lesion region.

It is to be explained that the organ part indicated by the organ information corresponds to multiple target endoscope images, and therefore, the target endoscope image adapted to the photographing mode can be obtained from the multiple target endoscope images obtained by photographing on the organ part, to localize the lesion region on the target endoscope image and identify the lesion category of the lesion region for the organ part.

The photographing mode aims at the target endoscope image that images the organ part. Exemplarily, the photographing mode includes the image type, dyeing type, etc. For example, the photographing mode includes three modes of white light, NBI, and iodine dyeing. For imaging the organ part, different lesion conditions on the target endoscope image are adapted to different photographing modes.

For example, normally, the white light mode is adopted, and when a suspicious lesion or a disease lesion region exists on the organ part, the white light mode is switched to the NBI mode. Since the image colors, textures, and details corresponding to the target endoscope images in different photographing modes are greatly different, through switching the photographing mode, the lesion region can be more accurately localized, so as to identify the lesion category of the lesion region.

After recognizing the target endoscope image to obtain the image type to which the target endoscope image is adapted, according to the identified image type, the corresponding photographing mode is determined, so as to directly switch the target endoscope image into the determined photographing mode, thereby obtaining the target endoscope image in the photographing mode to which the organ part where the endoscope is currently located is adapted, so as to enhance the accuracy of the image content represented by the target endoscope image. Through the exemplary embodiment, dynamic adjustment is performed on the photographing mode for the target endoscope image, so as to enhance the accuracy rate of image recognition.

In the photographing mode to which the organ part where the endoscope is located is adapted, localizing the lesion region of the target endoscope image and identifying the lesion category thereof can greatly improve the system performance and accuracy rate of the recognition result.

Through the execution of step 350, the organ information is obtained; the organ information corresponds to the target endoscope image obtained by filtering out the low-quality image; based on the organ information, localizing the lesion region of the target endoscope image and identifying the lesion category thereof can be performed in the adapted mode. The target endoscope image obtained by filtering out the low-quality image corresponding to the organ information can have the following two meanings: on one hand, the target endoscope image obtained by filtering out the low-quality image has been adapted to the photographing mode suitable for the current alimentary canal part; for example, the adapted photographing mode is the white light mode, while the target endoscope image obtained by filtering out the low-quality image corresponds to the white light mode, which is consistent with the photographing mode that needs to be used. On the other hand, the target endoscope image obtained by filtering out the low-quality image has a photographing mode that is not adapted to the photographing mode suitable for the organ part, for example, the photographing mode used by the endoscope image is the white light mode, while the photographing mode needing to be used is the NBI mode. Hence, it is required to switch the photographing mode of the target endoscope image.

Exemplarily, the executed lesion region localization and lesion category identification are both implemented by using a deep learning network. The lesion region localization may adopt a localization detection network, for example, and end-to-end real-time target location network YOLO (You Only Look Once, a deep learning network for target detection), and may also adopt other detection networks (e.g., FasterRCNN); the lesion category identification is implemented using the classification network; this classification network may be a Densely Connected Convolutional network (DenseNet for short).

It is to be further explained that a localization detection network deployed for the lesion region localization may be deployed uniformly. For example different organs use the same localization detection network, and the localization detection network may be separately deployed according to corresponding organ information, such as the alimentary canal parts. Moreover, the classification network deployed for the lesion category identification is also like this, and is determined according to experimental effects. If the network is separately deployed according to the alimentary canal parts, there is only a need to train the deep learning network separately.

Through the exemplary embodiment as stated above, a more complete and available medical endoscope image recognition system with strong robustness can be implemented, so as to comprehensively assist a doctor in diagnosis in many respects and improve diagnosis efficiency. Localizing the lesion region of the target endoscope image and identifying the lesion category thereof effectively can help avoid missed diagnosis of the alimentary canal examination by the endoscope, effectively assist the doctor to determine the lesion property in real time, and improve the accuracy rate of the determination.

In addition, using the neural network to filter the low-quality image for the endoscope image effectively can improve a noise proof capability and also improve the system availability.

The medical endoscope image recognition according to the exemplary embodiment above is implemented by means of deep learning, manual intervention is no longer needed for profound understanding of the medical image, and a manually made feature extraction solution is no longer needed as well, thereby avoiding omission and erroneous judgment caused by incomplete feature extraction.

Figure 4:
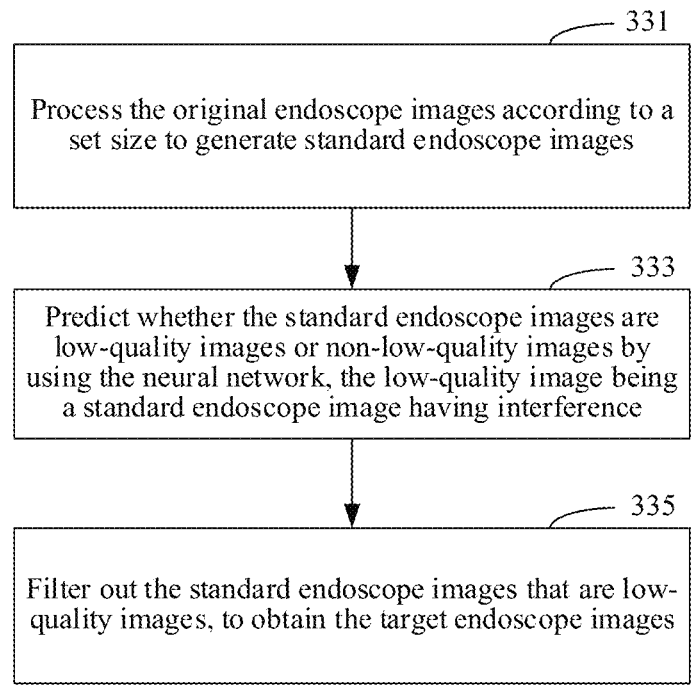
FIG. 4 is a flowchart of step 330 according to the embodiment corresponding to FIG. 3.

FIG. 4 is a flowchart of step 330 according to the embodiment corresponding to FIG. 3. In an exemplary embodiment, as shown in FIG. 4, step 330 includes at least the following steps.

In step 331, the original endoscope images are processed according to a set size to generate standard endoscope images.

The standard endoscope image is adapted to the endoscope image with the size required by the neural network for the neural network to be inputted. For recognition and filtering of the low-quality image facing the original endoscope image, first, it is required to pre-process the data, such as adjusting the size of the obtained original endoscope image, so that the generated standard endoscope image can be adapted to the input to the neural network and the consistency is ensured.

For example, according to the set size, the process of processing the original endoscope images includes: first executing a resize operation, and then using an image scaling method, such as a center crop method (a rounded corner cutting method) to cut, to obtain the standard endoscope image with the set size.

The resize operation is an adjusting operation for the original endoscope image; exemplarily, the execution process of the resize operation may be: maintaining a length-width ratio, scaling a short edge to 224 pixels, and a long edge being greater than or equal to 224 pixels. The execution process of the center crop method may be: using a long edge of the original endoscope image as a standard, and cutting a central region of the original endoscope image, so that the long edge becomes 224, so as to obtain a standard endoscope image conforming to the set size, to ensure the consistency of network prediction.

In step 333, prediction of whether the standard endoscope images are low-quality images or non-low-quality images is performed by using the neural network. The low-quality image is a standard endoscope image having interference for example.

In the real hospital usage environment, there can be many types of low-quality images, including vague, abnormally colored, and/or over-exposed unqualified images. Based on the unqualified images, the neural network is used for implementing a classification task, so as to filter the low-quality images of the standard endoscope images. Exemplarily, the neural network may be a deep convolutional neural network, such as Densenet.

Taking the standard endoscope image processed to the set size as an input, prediction of the low-quality image and non-low-quality image is performed by using the trained neural network, so as to output, by the neural network, a probability for the standard endoscope image to be the low-quality image and a probability for the standard endoscope image to be the non-low-quality image, and finally determine whether the standard endoscope image is the low-quality image or the non-low-quality image, so as to obtain the target endoscope images. In this exemplary embodiment, accordingly, the target endoscope image is an endoscope image adapted to the neural network and subjected to the size processing on the original endoscope image.

The trained neural network is constituted by executing the network training process after a large quantity of original endoscope images are divided into the low-quality images and the non-low-quality images. In an exemplary embodiment, the large quantity of original endoscope images as examples can be obtained by expanding the original endoscope images, so as to provide more samples for the training of the neural network.

In step 335, the standard endoscope images that are low-quality images are filtered out to obtain the target endoscope images.

After the original endoscope image obtained from the medical endoscope video stream is processed and predicted based on the steps above, the endoscope image corresponding to the low-quality image in the original endoscope images can be determined. In this case, the original endoscope image that is the low-quality image can be filtered out, which can effectively prevent useless and unnecessary images from entering the follow-up recognition process of the medical endoscope image.

Through this exemplary embodiment as stated above, recognition and filtering of the low-quality image are implemented for the medical endoscope image recognition, so as to be actually applied to a real production environment, such as a hospital, without influencing from the switching and shaking of the endoscope in the tract, and also without the influences from various liquids and foreign matters encountered in the tract by the endoscope.

Figure 5:
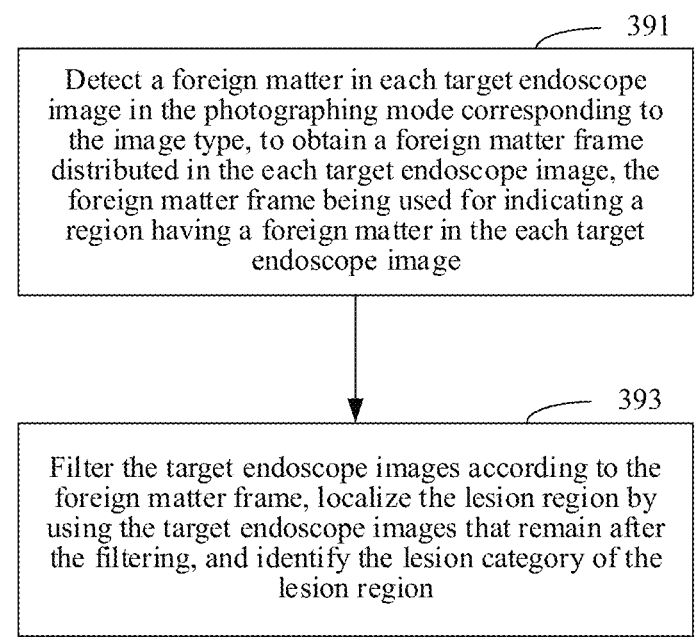
FIG. 5 is a flowchart of step 390 according to the embodiment corresponding to FIG. 3.

FIG. 5 is a flowchart of step 390 according to the embodiment corresponding to FIG. 3. In an exemplary embodiment, as shown in FIG. 5, step 390 includes the following steps.

In step 391, a foreign matter in each target endoscope image in the photographing mode corresponding to the image type is detected, to obtain a foreign matter frame distributed in the each target endoscope image, the foreign matter frame being used for indicating a region having a foreign matter in the each target endoscope image.

In step 393, the target endoscope images are filtered according to the foreign matter frame, the lesion region is localized by using the target endoscope images that remain after the filtering, and the lesion category of the lesion region is identified.

For the target endoscope image in the photographing mode corresponding to the adapted image type, before localizing the lesion region and identifying the lesion category, the foreign matters in the target endoscope image are further detected and localized, so as to filter out the foreign matters that influence the image content in the target endoscope image.

It is to be understood, taking an alimentary canal as an example, in the alimentary canal, there are often special intraoperative instruments, saliva and other foreign matters in the esophagus and stomach. Moreover, the image content of the target endoscope image captured by the endoscope in the alimentary canal can mostly contain intraoperative instruments, saliva and other foreign matters. Hence, the target endoscope image in which the foreign matter is detected cannot be directly filtered out.

In this case, it is necessary to estimate whether the existing foreign matter would interfere with the follow-up lesion region localization of the target endoscope image according to the distribution of the foreign matter in the target endoscope image; filtering out the target endoscope images with high foreign matter interference improves the noise proof capability of the system and enhances availability of image recognition.

For example, the detection of the foreign matter faces the target endoscope image adapted to the photographing mode; for this target endoscope image, the neural network is used for detecting the foreign matter in the image, and obtaining a foreign matter frame localized on the target endoscope image.

The foreign matter frame is used for indicating a region occupied by the foreign matter in the target endoscope image. It is to be understood that the foreign matter frame annotates the distribution of the foreign matter in the target endoscope image. The foreign matter frame is substantially a region occupied by the intraoperative instruments or a region occupied by the saliva.

Through foreign matter detection, the obtained foreign matter frame distributed on the target endoscope image is represented in the form of coordinates. This process implements the detection of the target by using the neural network; and under the action of the neural network, in addition to outputting the coordinates representing the foreign matter frame, a confidence of the foreign matter frame corresponding to the foreign matter is further outputted, such as the probability.

Exemplarily, for a foreign matter, if the foreign matter frame corresponding to the foreign matter is a square frame, the coordinates of the foreign matter may be determined by the square frame, and may include four pieces of coordinate information, such as x min, y min, x max, and y max.

After performing the foreign matter detection on the target endoscope image to obtain the foreign matter frame distributed in the target endoscope image, the foreign matter frame distributed in the target endoscope image can be used for evaluating whether to filter out the target endoscope image to shield the interference caused by excess foreign matters.

In an exemplary embodiment, step 391 includes: inputting the each target endoscope image in the photographing mode corresponding to the image type into the neural network, performing target detection by using the neural network, and outputting coordinates and a confidence that correspond to the foreign matter frame, where the coordinates are used for indicating a distribution of the foreign matter frame in the each target endoscope image.

The neural network for foreign matter detection may be a YOLO location network, and may also be another deep detection network, which is not limited herein. By using the deployed neural network, the entire target endoscope image is used as an input, the location of the foreign matter frame is regressed at an output layer, such as the coordinates and the category thereof, and this category is the foreign matter. That is, the confidence outputted by the neural network represents the possibility that the foreign matter corresponds to the localized foreign matter frame.

Figure 6:
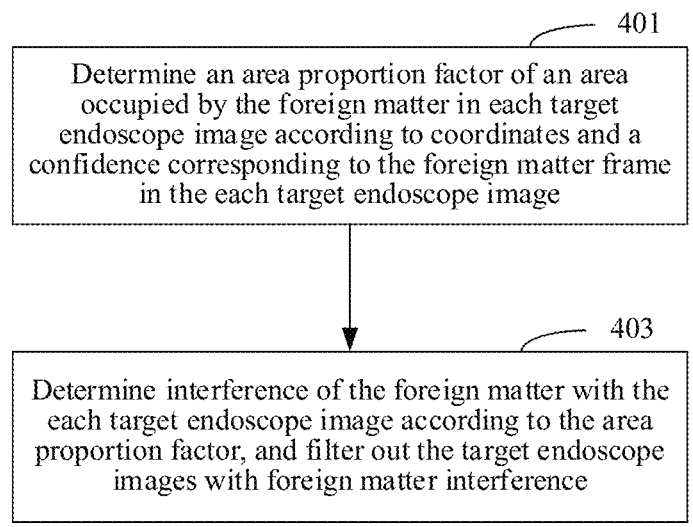
FIG. 6 is a flowchart of step 393 according to the embodiment corresponding to FIG. 5.

Further, in an exemplary embodiment, FIG. 6 is a flowchart of step 393 according to the embodiment corresponding to FIG. 5. Step 393, as shown in FIG. 6, includes the following steps.

In step 401, an area proportion factor of an area occupied by the foreign matter in each target endoscope image is determined according to the coordinates and the confidence corresponding to the foreign matter frame in the each target endoscope image.

After obtaining the coordinates and confidence corresponding to the foreign matter frame in the target endoscope image through foreign matter detection, according to the coordinates and the confidence, the area proportion factor of all foreign matters on the target endoscope image is calculated.

Exemplarily, a foreign matter frame area Si is first calculated according to the coordinates. The foreign matter frame area is an area occupied by the foreign matter frame. Then a corresponding confidence Pi is used as a coefficient to correct the foreign matter frame area, such as PiSi, and finally corrected foreign matter frame areas of all the foreign matter frames are added, such as by summing the area PiSi of each foreign matter frame, and performing a proportion calculation on the sum and a total area of the target endoscope image, to finally obtain the area proportion factor of the area occupied by the foreign matter in the target endoscope image.

In an exemplary embodiment, the area proportion factor corresponding to the target endoscope image may be calculated through the following formula:

$$f = \frac{\sum P_i S_i}{HW}$$

where f is the area proportion factor; H is the height of the target endoscope image; W is the width of the target endoscope image; i is an identifier of the foreign matter frame; the value of i is greater than or equal to 1; $P_i$ is the confidence of the ith foreign matter frame, that is $P_i$=confidence, $S_i$ is the area of the ith foreign matter frame, $S_i=(x_{maxi}-x_{mini})*(y_{maxi}-y_{mini})$.

In step 403, interference of the foreign matter with the each target endoscope image is determined according to the area proportion factor, and filter out the target endoscope images with foreign matter interference.

After obtaining the area proportion factor of the area occupied by the foreign matter in the target endoscope image through calculation, the interference of the foreign matter with the each target endoscope image can be determined according to the numeral value of the area proportion factor. As can be understood, the greater the numeral value of the area proportion factor is, the interference with the target endoscope image is greater; the smaller the numeral value of the area proportion factor is, the interference with the target endoscope image is tinier, and the less influence is caused to the following lesion region localization and category identification of the target endoscope image.

Hence, target endoscope images with relatively larger area proportion factors are filtered out, and these images are considered to be the target endoscope images with the foreign matter interference.

In an exemplary embodiment, a threshold $f_0$ is first set, and the default value of $f_0$ may be 0.1. When f is greater than the threshold $f_0$, it is determined that the target endoscope image is the target endoscope image with foreign matter interference, and the target endoscope image needs to be filtered out.

When f is smaller than the threshold $f_0$, lesion region localization for the target endoscope image and lesion category identification for the localized lesion region are continued.

Through this exemplary embodiment, foreign matter localization and anti-inference are implemented, so as to resolve the special foreign matter problems such as intraoperative instruments and saliva in the esophagus and stomach in the alimentary canal, thereby reducing the influence on image recognition due to the presence of the foreign matter.

Figure 7:
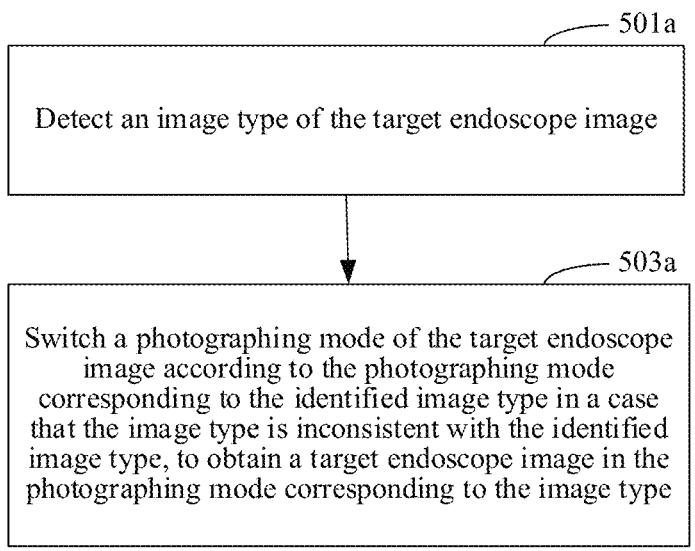
FIG. 7 is a flowchart of step 390 according to the embodiment corresponding to FIG. 3.

FIG. 7 is a flowchart of step 390 according to the embodiment corresponding to FIG. 3. In an exemplary embodiment, as shown in FIG. 6, step 390 at least includes the following steps.

In step 501a, an image type of the target endoscope image is detected.

In step 503a, a photographing mode corresponding to the target endoscope image is switched according to the photographing mode corresponding to the identified image type when the image type is inconsistent with the identified image type, to obtain a target endoscope image in the photographing mode corresponding to the image type.

After obtaining the image type suitable for the target endoscope images through recognition, according to the image type of the target endoscope image, whether to switch the photographing mode can be estimated, to ensure that the photographing mode of the target endoscope image is suitable.

For example, only when the image type of the target endoscope image is inconsistent with the image type obtained through recognition, the photographing mode of the target endoscope image is switched to obtain the target endoscope image in the photographing mode corresponding to the image type suitable for the target endoscope images.

Figure 8:
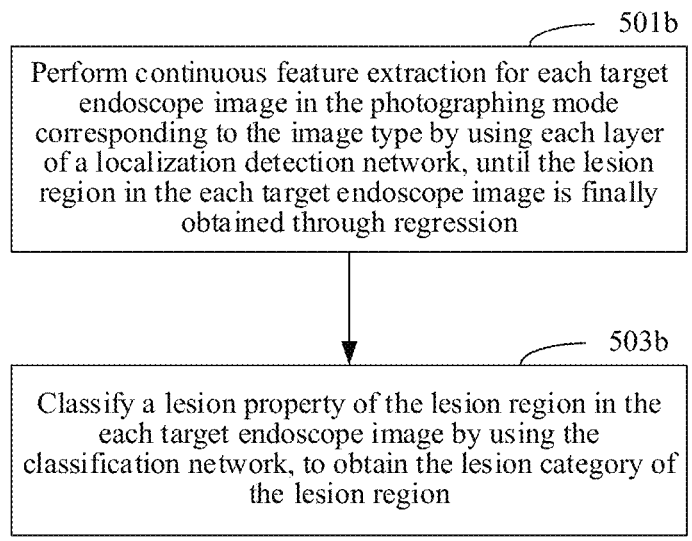
FIG. 8 is a flowchart of step 390 according to the embodiment corresponding to FIG. 7.

FIG. 8 is a flowchart of step 390 according to the embodiment corresponding to FIG. 3. In an exemplary embodiment, as shown in FIG. 8, step 390 includes the following steps.

In step 501b, continuous feature extraction for each target endoscope image in the photographing mode corresponding to the image type is performed by using each layer of a localization detection network until the lesion region in the each target endoscope image is finally obtained through regression.

In step 503b, a lesion property of the lesion region in the each target endoscope image is classified by using the classification network, to obtain the lesion category of the lesion region.

The localization detection network is used for performing target detection on the target endoscope image, to implement the lesion localization in the target endoscope image, so as to output two-dimensional coordinates of the lesion region.

Exemplarily, the localization detection network is an end-to-end real-time target detection algorithm, such as YOLO, to meet real-time requirements for image recognition. The localization detection network may also use other detection networks for replacement, such as FasterRCNN.

A process of performing continuous feature extraction by using each layer of the localization detection network to obtain the lesion region in the each target endoscope image through regression obtains more features and is more comprehensive, and thus can avoid incomplete feature extraction and omission and misjudgment caused thereby.

In an exemplary embodiment, the lesion region obtained upon location detection would be represented in the form of two-dimensional coordinates. The localization detection network finally outputs the two-dimensional coordinates for localizing the lesion region on the target endoscope image.

For example, the localization problem of the lesion region by the YOLO relates to the extraction image bounding boxes and category probability regression problems. At this point, through the continuous feature extraction in each layer of the network, the two-dimensional coordinates and probability are finally obtained by regression, and therefore, the accuracy of localization is improved while ensuring the real-time performance of the detection.

For the localization detection network for implementing the lesion region localization, in an exemplary embodiment, network training is performed using an image data set with an open source, so as to obtain parameters and weight values of each network layer, for example, the parameters and weight values of the convolution layer can be obtained, so as to construct a localization detection network having more generalization performance. The data amount of the image data set with an open source is above a million; training the localization detection network using the image data set with an open source may avoid overfitting, so that the network training can be better converged to an optimal point.

In addition, the low-quality image is also added into the training process of the localization detection network. For example, based on the low-quality endoscope image, training the localization detection network, to enhance the robustness and anti-noise capability of the localization detection network and to reduce a false positive ratio.

After localizing the lesion region, the recognition of the lesion category of the lesion region can be executed. Exemplarily, the category may include normal, precancerous disease lesion, early cancer, advanced cancer, inflammatory disease lesion, and other disease lesions, which are not limited herein.

In an exemplary embodiment, the classification network implementing the lesion category identification may be based on Densenet. The input of the classification network is a lesion region in the target endoscope image, and the output thereof is the lesion category corresponding to the lesion region.

At this point, the lesion region localization and lesion region recognition can implement a more complete and available image recognition solution, without being limited to a single function, ensuring the comprehensiveness of the supported functions.

Figure 9:
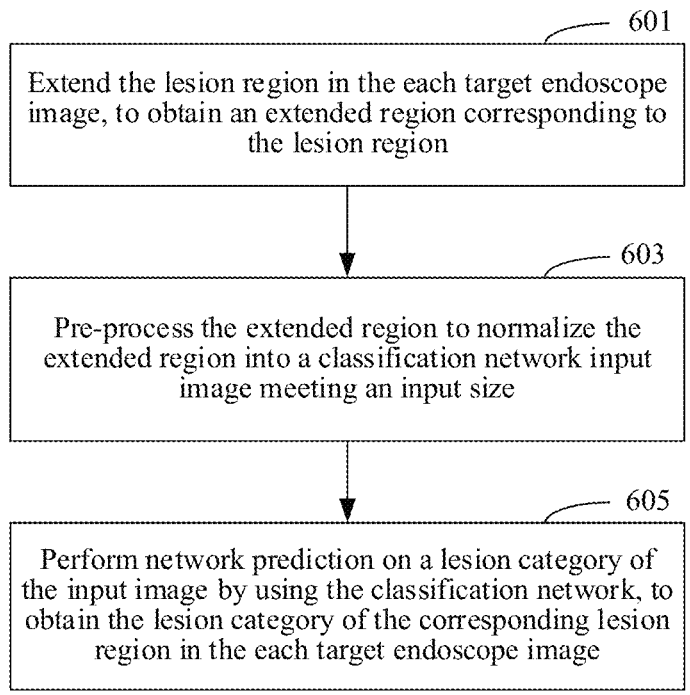
FIG. 9 is a flowchart of step 503b according to the embodiment corresponding to FIG. 3.
Figure 10:
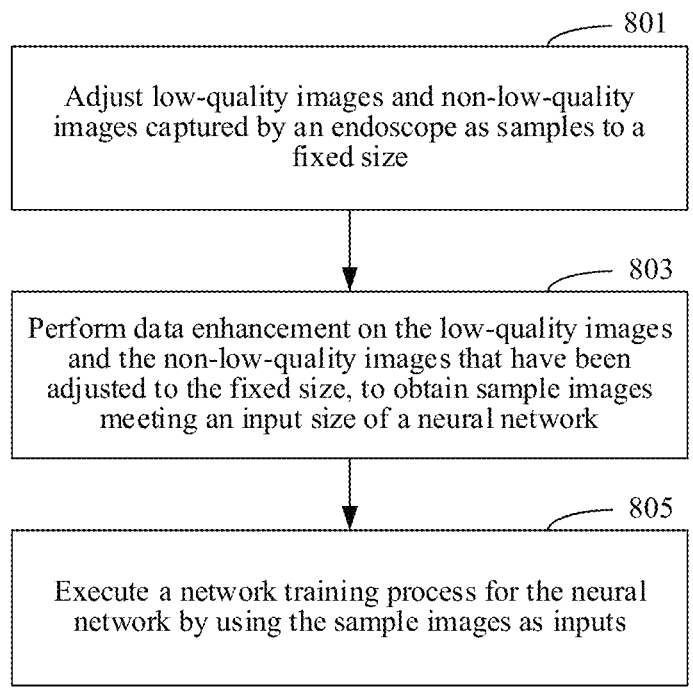
FIG. 10 is a flowchart of a step of training a neural network by using low-quality images and non-low-quality images captured by an alimentary canal endoscope as samples, to obtain a neural network corresponding to a low-quality image category output probability and a non-low quality image category output probability according to an exemplary embodiment.

FIG. 9 is a flowchart of step 503b according to the embodiment corresponding to FIG. 8. In an exemplary embodiment, as shown in FIG. 10, step 503b includes the following steps.

In step 601, the lesion region in the each target endoscope image is extended, to obtain an extended region corresponding to the lesion region.

As can be understood, the localized lesion regions in the target endoscope image are not consistent with each other in size. For example, for each lesion region, the lesion region is first extended so as to obtain an extended region corresponding to each lesion region subjected to the lesion category identification.

The external expansion of the region can ensure that the lesion region for recognition can obtain certain context semantic information. Features related to lesions often exist around the lesion region. For example, the lesion is not strictly provided with a boundary, and the lesion is a gradually changed process. Therefore, the external expansion of the region can provide more information to the classification network to learn, so as to avoid missing useful boundary information.

In an exemplary embodiment, the external expansion of the lesion region is a process of setting the proportions of up, down, left, and right external expansion of this lesion region. For example, the lesion region is extended by 10% upwards, downwards, leftwards, and rightwards.

In step 603, the extended region is pre-processed to normalize the extended region into a classification network input image meeting an input size.

The extended region is pre-processed so that the extended region is normalized as an image with the input size, so as to ensure the input of the classification network may be met.

In an exemplary embodiment, the pre-processing process includes an execution process using a center crop method. Moreover, the classification network training process corresponding thereto requires to implement the pre-processing of the classification network input image through a data enhancing method, so as to expand the samples.

In step 605, network prediction on a lesion category of the input image is performed by using the classification network, to obtain the lesion category of the corresponding lesion region in the each target endoscope image.

After obtaining the image of the extended region including the context information through the preceding steps, the image is inputted into the classification network, so that network prediction of the lesion category can be performed on the corresponding lesion region; in a similar fashion, the lesion category of the lesion region in the endoscope image can be identified.

Exemplarily, the classification network for implementing category identification may be a Densenet model. The lesion categories outputted by the classification network may be six categories, such as normal, precancerous disease lesion, early cancer, advanced cancer, inflammatory disease lesion, and other disease lesions. In this case, the classification network is actually a six-class network.

Identifying the lesion category of the lesion region in the endoscope image can output in real time the specific property of the lesion of the alimentary canal through image recognition in the alimentary canal detection process of the endoscope, so as to assist the doctor in the alimentary canal endoscope image diagnosis.

In an exemplary embodiment, a medical endoscope image recognition method further includes training a neural network by using low-quality images and non-low-quality images captured by an endoscope as samples, to obtain a neural network corresponding to a low-quality image category output probability and a non-low quality image category output probability. The neural network is used for generating target endoscope images. Corresponding to the preceding description, the endoscope image may be the original endoscope image, and may be a standard endoscope image matched with the neural network size processing, which is not limited herein.

As described above, for the original endoscope image obtained from the medical endoscope video stream, recognizing, by using the trained neural network, whether it is a low-quality image, so as to filter out the endoscope image corresponding to the low-quality image, avoids the occurrence of noise that is useless and may influence the processing efficiency.

FIG. 10 is a flowchart of a step of training a neural network by using low-quality images and non-low-quality images captured by an endoscope as samples, to obtain a neural network corresponding to a low-quality image category output probability and a non-low quality image category output probability according to an exemplary embodiment. In an exemplary embodiment, as shown in FIG. 10, the steps include the following steps.

In step 801, the low-quality images and the non-low-quality images captured by the endoscope as the samples are adjusted to a fixed size.

In step 803, data enhancement is performed on the low-quality images and the non-low-quality images that have been adjusted to the fixed size, to obtain sample images meeting an input size of a neural network.

In step 805, a network training process for the neural network is executed by using the sample images as inputs.

First it is to be explained, the sample of the neural network for recognizing the low-quality image includes the low-quality image and non-low-quality image captured by the endoscope, but is not limited to the low-quality image and non-low-quality image captured by the endoscope, and further includes images expanded from the low-quality image and non-low-quality image captured, so as to form the sample image inputted to the neural network.

The low-quality image and non-low-quality image captured by the endoscope are not obtained by one endoscope examination but are endoscope images widely obtained through various modes.

For the network training process, parameters and weight values of each network layer are obtained through a large scale of sample inputs, and the data amount of the sample also determines the generalization performance and classification accuracy of the trained neural network. Hence, for the low-quality image and non-low-quality image captured by the endoscope, while performing size adjustment according to the input requirements of the neural network, it is also needed to continuously expand the data amount of the sample, such as by performing data enhancement on the image upon completed size adjustment, to obtain more sample images.

The executed fixed-size adjustment is the process of adjusting the image to a fixed size, for example, the process of adjusting the image to 227*227 pixels. Moreover, data enhancement is data pre-processing using a random cutting method, etc. and combining a series of operations such as random rotation, brightness, color, contrast, and random jitter to perform fixed-size adjustment and data enhancement on the low-quality images and the non-low-quality images, so as to obtain various images, for example, images at different angles, to enhance the generalization performance and prevent the occurrence of the overfitting phenomenon.

Data enhancement is performed on each of the low-quality images and the non-low-quality images, to change one image into multiple images, so as to together form sample images meeting the input size of the neural network.

Through the exemplary embodiment, the sample data can be expanded for the network training process; on the basis of the existing low-quality image and non-low-quality image captured by the endoscope, sufficient sample data may be provided to implement the network training process of converging to the optimal point.

Through the exemplary embodiment as stated above, real-time image recognition of each original endoscope image is performed for the endoscope photographing, and it can implement the accurate and rapid capture of the lesion in the endoscope examination while having the real-time performance.

Now at the angle of executing the alimentary canal endoscope examination, it is elaborated by combining the method implementation above.

During the process for a doctor to use the endoscope to examine the alimentary canal, the video stream is inputted, such as the medical endoscope video stream of the alimentary canal, while executing the current image display synchronously, the original endoscope image is correspondingly obtained.

At this time, a series of processes of low-quality image recognition and filtering, alimentary canal part localization, lesion region localization, and category identification would be performed on the original endoscope image, and therefore, real-time and accurate assistance is continuously provided in the endoscope examination, to rapidly provide complete and accurate processing on the generation of a large quantity of original endoscope images during the alimentary canal photographing process of the endoscope, so that the generation of the large quantity of medical images would no longer be a bottleneck of the alimentary canal endoscope examination.

Figure 11:
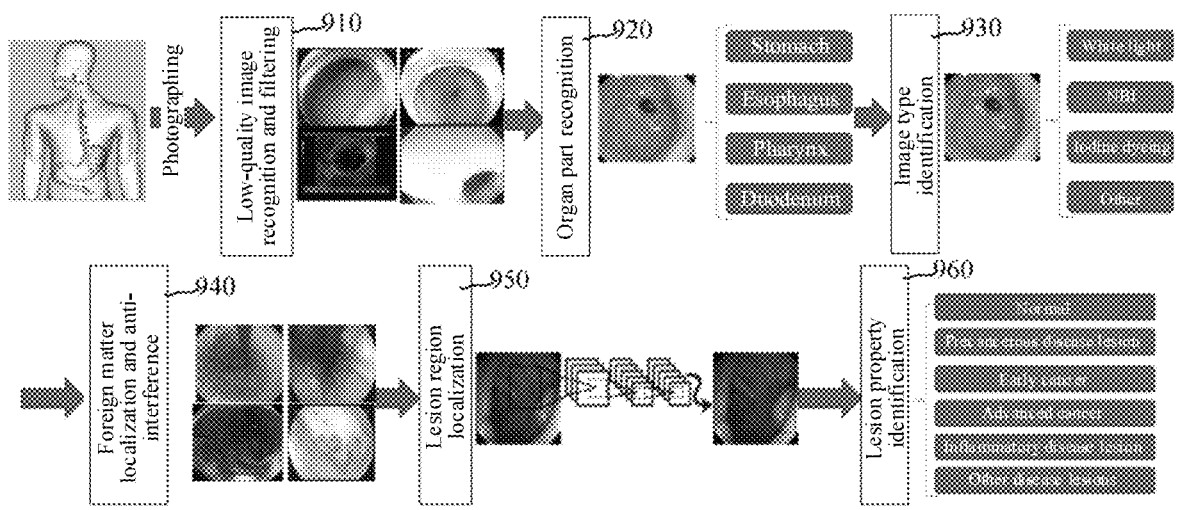
FIG. 11 is a schematic diagram of an overall framework of image recognition under photographing by an alimentary canal endoscope according to an exemplary embodiment.

For example, FIG. 11 is a schematic diagram of an overall framework of image recognition photographed by the alimentary canal endoscope according to an exemplary embodiment. In an application of an exemplary embodiment, as shown in FIG. 11, in the process of photographing the alimentary canal using the endoscope, along with the movement and photographing of the endoscope in the alimentary canal, the medical endoscope video stream of the alimentary canal is outputted.

For the medical endoscope video stream of the alimentary canal, step 910 is first executed to perform recognition and filtering on the low-quality image on each original endoscope image to remove the original endoscope image belonging to the low-quality image to generate the target endoscope image.

At this point, it is to be further indicated that for the recognition and filtering of the low-quality image as the classification task, Densenet can be selected to construct the neural network to be used, and in the execution process of the neural network, the sample is processed through the data enhancing method, but for the network prediction process, the data enhancing method is no longer executed, only a single cutting method, for example, the center crop method, is used for ensuring consistency, so as to avoid the increase of time consumption caused by the data enhancement, ensuring the real-time performance.

Filtering the low-quality image through step 910 can effectively remove the low-quality image in the original endoscope image so that the non-low-quality image can execute the following image recognition process.

For the target endoscope image, step 920 is executed to recognize the organ part. Moreover, for the organ part recognition as the classification task, the Densenet can also be selected to construct the neural network to be used, such as the preceding indicated four-class network.

Through recognizing the organ part of the endoscope image, the organ part where the endoscope is currently located in the alimentary canal can be localized in the process of continuous movement and photographing of the endoscope, so as to provide a proper available photographing mode for the endoscope that photographs the organ part.

Different photographing modes correspond to different image types, and therefore, the image type identification in step 930 is substantially the identification of the photographing mode suitable for the endoscope image. After recognizing to obtain the image type that is to be set for the endoscope image, the photographing mode of the endoscope image can be switched according to this image type, thereby obtaining the photographing mode suitable for the endoscope image for each endoscope image obtained by filtering out the low-quality image.

Figure 12:
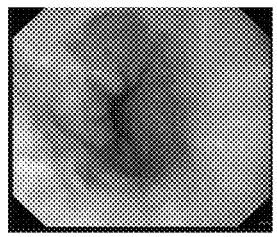
FIG. 12 is a schematic diagram of an endoscope image in a white light photographing mode according to an exemplary embodiment.
Figure 13:
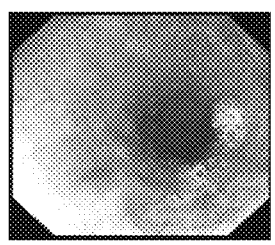
FIG. 13 is a schematic diagram of an endoscope image in an NBI mode according to the embodiment corresponding to FIG. 12.
Figure 14:
FIG. 14 is a schematic diagram of an endoscope image in an iodine dyeing mode according to the embodiment corresponding to FIG. 12.

For example, FIG. 12 is a schematic diagram of an endoscope image in a white light photographing mode according to an exemplary embodiment. FIG. 13 is a schematic diagram of an endoscope image in an NBI mode according to the embodiment corresponding to FIG. 12. FIG. 14 is a schematic diagram of an endoscope image in an iodine dyeing mode according to the embodiment corresponding to FIG. 12.

As can be seen from FIG. 12 to FIG. 14, the image colors, textures, and details of the three images are greatly different, and therefore, in the process of recognition, adaptively switching the photographing mode upon recognition of the image type greatly enhances the accuracy of image recognition.

In step 930, the image type is identified. The step also needs to implement the classification task. Hence, the Densenet model can also be selected to construct the classification network to be used, such as the three-class network, and therefore, the network training process thereof is similar to the training process of the low-quality image filtering network.

After obtaining the target endoscope image in the photographing mode suitable for the alimentary canal part where the endoscope is currently located after completing the image type identification, the foreign matter localization and anti-interference implementing processes in step 940 are executed, to eliminate the interference of the foreign matter, so as to complete the lesion region localization and the lesion category identification. Through the execution process stated above, an endoscope image frame would be processed in an average of 150 milliseconds, which meets the real-time performance requirement, and has very high accuracy. The implementation of the execution process can be deployed to a hospital, so as to assist a doctor in diagnosis of the alimentary canal endoscope image in real-time, improving the diagnosis efficiency of the doctor.

Based on the execution process stated above, a more complete and available system with strong robustness for assisting the alimentary canal endoscope examination can be implemented, so as to more comprehensively implement assistance; in the processing of the endoscope image, the smoothness of a video frame rate can be ensured, for example, an average of less than 150 milliseconds per frame.

Through the execution process stated above, the alimentary canal endoscope diagnosis system directly applied to a hospital production environment is obtained, and under the current situation of scarce and uneven medical resources, the system can assist the doctor to localize and discover the alimentary canal lesion, and prevent misdiagnosis.

Apparatus embodiments of this disclosure are described below, and can be used to perform the embodiments of the foregoing medical endoscope image recognition method of this disclosure. For details not disclosed in the apparatus embodiments of this disclosure, refer to the embodiments of the medical endoscope image recognition method of this disclosure.

Figure 15:
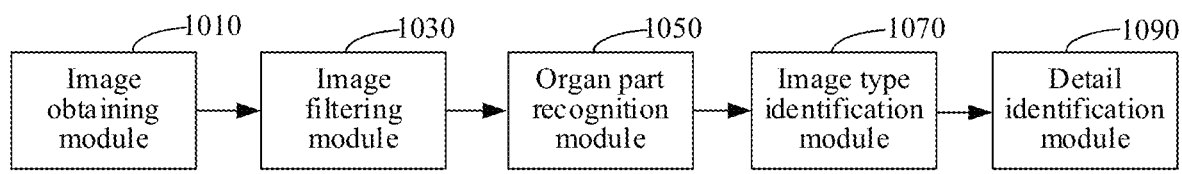
FIG. 15 is a block diagram of a medical endoscope image recognition system according to an exemplary embodiment.

FIG. 15 is a block diagram of a medical endoscope image recognition system according to an exemplary embodiment. In an exemplary embodiment, as shown in FIG. 15, the physical medical endoscope image recognition system includes, but is not limited to: an image obtaining module 1010, an image filtering module 1030, an organ part recognition module 1050, an image type identification module 1070, and a detail identification module 1090. One or more modules, submodules of the apparatus can be implemented by processing circuitry, software, or a combination thereof, for example.

The image obtaining module 1010 is configured to obtain original endoscope images according to a medical endoscope video stream.

The image filtering module 1030 is configured to filter the original endoscope images by using a neural network, to generate target endoscope images.

The organ part recognition module 1050 is configured to recognize organ information corresponding to the target endoscope images by using the neural network.

The image type identification module 1070 is configured to identify an image type suitable for the target endoscope images according to the corresponding organ information by using a classification network.

Further, the detail identification module 1090 is configured to localize a lesion region in each of the target endoscope images according to a part indicated by the organ information, and identify a lesion category of the lesion region in a photographing mode corresponding to the image type.

In some embodiments, this disclosure further provides a machine device. The machine device may be applied to the implementation environment in FIG. 1, to perform all or some of the steps in the method shown in any one of FIG. 3, FIG. 5, FIG. 6, FIG. 8, FIG. 9, and FIG. 10. The apparatus can include a processor and a memory. The memory is configured to store processor executable instructions. The processor is configured to implement one or more of the foregoing methods.

Exemplary implementations of operations performed by the processor of the apparatus in this embodiment are described in detail in the foregoing embodiments. Details are not described herein.

It is to be understood that this disclosure is not limited to the precise structures described above and shown in the accompanying drawings, and various modifications and changes may be made without departing from the scope of this disclosure.

What is claimed is:

1. A medical endoscope image recognition method, comprising:
  receiving endoscope images from a medical endoscope;
  filtering the endoscope images with a first neural network, to obtain target endoscope images;
  recognizing organ information corresponding to the target endoscope images via a second neural network, the organ information indicating which organ is included in each of the target endoscope images;

identifying an imaging type of the target endoscope images according to the corresponding organ information with a first classification network;

localizing a lesion region in the target endoscope images according to the organ indicated by the organ information; and identifying, by processing circuitry, a lesion category of the lesion region in an image capture mode of the medical endoscope corresponding to the imaging type.

2. The method according to claim 1, wherein the endoscope images are captured by the medical endoscope in a tract connected to outside a body or a sealed body cavity.

3. The method according to claim 1, wherein the receiving comprises:

receiving the endoscope images while the medical endoscope is being manipulated and capturing the endoscope images inside a body.

4. The method according to claim 1, wherein the receiving comprises:

receiving the endoscope images of a previously stored medical endoscope video stream, at least one of the endoscope images being used to recognize the lesion region in a tract or a sealed body cavity captured by the medical endoscope and identify the lesion category of the lesion region.

5. The method according to claim 1, wherein the filtering comprises:

processing the endoscope images according to a set size to generate standard endoscope images;

determining whether the standard endoscope images are low-quality images or non-low-quality images via the first neural network; and filtering out the standard endoscope images that are low-quality images, to obtain the target endoscope images.

6. The method according to claim 1, wherein the localizing comprises:

detecting foreign matter in each of the target endoscope images in the image capture mode corresponding to the imaging type, to obtain a foreign matter frame in the respective target endoscope image, the foreign matter frame indicating a region having the foreign matter in the respective target endoscope image;

filtering the target endoscope images according to the foreign matter frame; and localizing the lesion region with the filtered target endoscope images.

7. The method according to claim 6, wherein before the detecting the foreign matter, the localizing further comprises:

switching the image capture mode of the medical endoscope according to the identified imaging type, to obtain the target endoscope image in the image capture mode corresponding to the imaging type.

8. The method according to claim 6, wherein the detecting the foreign matter comprises:

inputting the target endoscope images in the image capture mode corresponding to the imaging type into a third neural network, performing target detection via the third neural network, and outputting coordinates and confidence levels that correspond to the foreign matter frames, the coordinates indicating positions of the foreign matter frames in the target endoscope images.

9. The method according to claim 6, wherein the filtering the target endoscope images according to the foreign matter frame comprises:

determining an area proportion factor of an area occupied by the foreign matter in each of the target endoscope images according to coordinates and a confidence level corresponding to the foreign matter frame in the respective target endoscope image;

determining whether the foreign matter interferes with the respective target endoscope image according to the area proportion factor; and filtering out the target endoscope images with the foreign matter interference.

10. The method according to claim 1, wherein the localizing includes performing continuous feature extraction of the target endoscope images in the image capture mode corresponding to the imaging type by using each layer of a localization detection network, until the lesion region in the target endoscope images is obtained through regression; and the identifying the lesion category includes classifying a lesion property of the lesion region in the target endoscope images with the classification network, to obtain the lesion category of the lesion region of the target endoscope images.

11. The method according to claim 10, wherein the classifying comprises:

extending the lesion region in a respective target endoscope image of the target endoscope images, to obtain an extended region corresponding to the lesion region of the respective target endoscope image;

pre-processing the extended region to normalize the extended region into a classification network input image meeting an input size; and performing network prediction on the lesion category of the input image via the classification network, to obtain the lesion category of the corresponding lesion region in the respective target endoscope image.

12. The method according to claim 1, further comprising:

training the first neural network by using low-quality images and non-low-quality images captured by a reference endoscope as samples, to obtain the first neural network corresponding to a low-quality image category output probability and a non-low quality image category output probability, the first neural network being configured to obtain the target endoscope images.

13. The method according to claim 12, wherein the training the first neural network comprises:

adjusting the low-quality images and the non-low-quality images captured by the reference endoscope as the samples to a fixed size;

performing data enhancement on the low-quality images and the non-low-quality images that have been adjusted to the fixed size, to obtain adjusted sample images meeting an input size of the first neural network; and executing a network training process for the first neural network by using the adjusted sample images as inputs.

14. The method according to claim 1, wherein the second neural network includes a second classification network associated with the organ, and the classification network is obtained by training with sample endoscope images in which the organ is annotated.

15. A medical endoscope image recognition system, comprising:

processing circuitry configured to:

receive endoscope images from a medical endoscope;

filter the endoscope images with a first neural network, to obtain target endoscope images;

recognize organ information corresponding to the target endoscope images via a second neural network, the organ information indicating which organ is included in each of the target endoscope images;

identify an imaging type of the target endoscope images according to the corresponding organ information with a classification network;

localize a lesion region in the target endoscope images according to the organ indicated by the organ information; and identify a lesion category of the lesion region in an image capture mode of the medical endoscope corresponding to the imaging type.

16. The system according to claim 15, wherein the endoscope images are captured by the medical endoscope in a tract connected to outside a body or a sealed body cavity.

17. The system according to claim 15, wherein the processing circuitry is configured to:
receive the endoscope images while the medical endoscope is being manipulated and capturing the endoscope images inside a body.

18. The system according to claim 15, wherein the processing circuitry is configured to:
receive the endoscope images of a previously stored medical endoscope video stream, at least one of the endoscope images being used to recognize the lesion region in a tract or a sealed body cavity captured by the medical endoscope and identify the lesion category of the lesion region.

19. An endoscopic imaging system, comprising:
the medical endoscope image recognition system according to claim 15; and
a display device configured to display the endoscope images.

20. A non-transitory computer-readable storage medium, storing instructions which when executed by a processor cause the processor to perform:
receiving endoscope images from a medical endoscope;
filtering the endoscope images with a first neural network, to obtain target endoscope images;
recognizing organ information corresponding to the target endoscope images via a second neural network, the organ information indicating which organ is included in each of the target endoscope images;
identifying an imaging type of the target endoscope images according to the corresponding organ information with a classification network;
localizing a lesion region in the target endoscope images according to the organ indicated by the organ information; and
identifying a lesion category of the lesion region in an image capture mode of the medical endoscope corresponding to the imaging type.

* * * * *